United States Patent [19]

Dauplaise et al.

[11] Patent Number: 4,696,770

[45] Date of Patent: Sep. 29, 1987

[54] METHOD FOR THE SYNTHESIS OF SULFONATED RUBRENE

[75] Inventors: David L. Dauplaise, Norwalk; William J. Trzaskos, Ridgefield, both of Conn.

[73] Assignee: American Cyanamid Company, Stamford, Conn.

[21] Appl. No.: 607,843

[22] Filed: May 7, 1984

[51] Int. Cl.⁴ .............................................. C09K 11/06
[52] U.S. Cl. .................................. 252/700; 252/186.29
[58] Field of Search .............. 252/301.16, 700, 186.28, 252/186.29

[56] References Cited

U.S. PATENT DOCUMENTS

| | | | |
|---|---|---|---|
| 3,888,786 | 6/1975 | Maulding | 252/700 |
| 3,893,938 | 7/1975 | Rauhut | 252/700 |
| 3,970,660 | 7/1976 | Bollyky | 252/700 |
| 3,994,820 | 11/1977 | Maulding et al. | 252/700 |
| 4,313,843 | 2/1982 | Bollyky et al. | 252/700 |
| 4,366,079 | 12/1982 | Rauhut et al. | 252/700 |
| 4,407,743 | 10/1983 | Tseng | 252/700 |
| 4,462,931 | 7/1984 | Cohen et al. | 252/700 |

*Primary Examiner*—Deborah L. Kyle
*Assistant Examiner*—T. J. Wallen
*Attorney, Agent, or Firm*—Frank M. Van Riet

[57] ABSTRACT

An improved process for the production of sulfonated rubrene is disclosed whereby fuming sulfuric acid is employed as the sulfonating agent. The resultant sulfonated rubrene is used as a fluorescer in water-soluble chemiluminescent mixtures e.g. in combination with a water-soluble amide of oxalic acid and hydrogen peroxide or a source of hydrogen peroxide.

4 Claims, No Drawings

METHOD FOR THE SYNTHESIS OF SULFONATED RUBRENE

BACKGROUND OF THE INVENTION

The invention described herein was made in the performance of work supported by the Office of Naval Research (Contract No. N-00014-82-C-0202), and is subject to the provisions of DAR-7-104.6, December, 1969, and DAR-7-302.23(b) long form, July 1981.

Chemiluminescent systems based on organic solvent solutions have become commercially available in the past. The use of aqueous solvent systems have not been as successful because of decreased efficiencies until recently. U.S. Pat. No. 4,366,079, incorporated herein by reference, discloses such an aqueous chemiluminescent system wherein sulfonated rubrene is contacted with a water-soluble amide of oxalic acid. The sulfonated rubrene utilized in the production of such chemiluminescent systems is conventionally prepared by utilizing sulfur trioxide as the sulfonating agent as disclosed in Example 1 of the above-cited patent.

Although the use of sulfur trioxide has proven successful in the production of sulfonated rubrene, the process has resulted in the production of many side reaction products which must be eliminated in order that a satisfactory product can be recovered. Furthermore, the use of sulfur trioxide is rather expensive and at times can be dangerous and difficult to handle due to its corrosive and hygroscopic nature. Additionally, sulfonated rubrene, when using the sulfur trioxide process, is produced in relatively poor yields.

Accordingly, if a safe procedure for the production of sulfonated rubrene could be found wherein the yield of product is additionally enhanced and a less expensive recovery procedure could be followed, a step forward in the art would be achieved.

SUMMARY OF THE INVENTION

It has now been found that sulfonated rubrene can be prepared in higher yields, under safer conditions and with a less complex recovery procedure by the use of fuming sulfuric acid as the sulfonating agent.

DESCRIPTION OF THE INVENTION INCLUDING PREFERRED EMBODIMENTS

The present invention is directed to a process for the production of a sulfonated rubrene which comprises slowly charging an aqueous solution of fuming sulfuric acid to a solution of a rubrene in a solvent mixture of dioxane and at least one of ethylene dichloride and methylene dichloride, reacting the rubrene and the sulfuric acid for at least 12 hours.

Any rubrene may be sulfonated in accordance with the process of the present invention including, but not limited to, rubrene per se, and halo, alkyl, carboxy, alkoxy, hydroxy or aryloxy substituted rubrenes. The preferred rubrene is rubrene per se.

The rubrene is charged to the reaction vessel as a solution in dioxane and at least one other solvent selected from ethylene dichloride and methylene dichloride. It is preferred that both methylene dichloride and ethylene dichloride be used in conjunction with the dioxane, and even more preferred that the ratio of dioxane to ethylene dichloride to methylene dichloride be about 2:2:1, respectively.

The fuming sulfuric acid is charged to the reaction vessel containing the rubrene as an aqueous solution, preferably as a 10% to 25% solution, slowly over a period of from about 1-10 minutes. The reaction is allowed to proceed over a period of at least 12 hours, preferably from about 15-36 hours, i.e., with stirring, until sufficient sulfonation is achieved so as to render the rubrene water-soluble.

After the reaction is complete, the sulfonated rubrene is recovered by adding water to the reaction media, adjusting the pH to about 7.0, concentrating the resultant aqueous phase by distilling off the water, slurrying the resultant concentrated product in an alcohol, such as methanol, ethanol, etc., filtering the slurry and concentrating the filtered alcohol solution by distilling off the alcohol.

When a fluorescer produced by the process described above is mixed with the water-soluble amides of oxalic acid disclosed in the above-referenced U.S. Patent, and hydrogen peroxide or a source of hydrogen peroxide, the mixture produces a chemiluminescent emission of excellent efficiency due to the purity of the sulfonated rubrene i.e. the sulfonated rubrenes produced by the instant process are less contaminated by by-products etc. and therefore function more efficiently in the mixture. The same hydrogen peroxide producing compounds and amides of oxalic acid disclosed in the above-referenced U.S. patent can be used herein in similar molar concentrations and mole ratios.

The following examples are set forth for purposes of illustration only and are not to be construed as limitations on the present invention except as set forth in the appended claims. All parts and percentages are by weight unless otherwise specified.

EXAMPLE 1

To a suitable reaction vessel is added one part of rubrene in 80 ml. of dioxane, 80 ml. of ethylene dichloride and 40 ml. of methylene dichloride. Eighteen percent fuming sulfuric acid (0.5 ml) is added slowly over a period of five minutes. The reaction media is stirred for 24 hours and 300 ml. of water are then added and the pH is adjusted to 7.0 with sodium carbonate.

The media forms into two phases and the aqueous phase is separated and distilled until a solid product remains. The solid product is slurried in 300 ml of methanol and filtered. The filtered methanol solution is concentrated by distillation yielding 1.3 parts of water-soluble sulfonated rubrene.

EXAMPLE 2

Aqueous hydrogen peroxide containing sodium salicylate is added to a suitable vessel containing a mixture of the sulfonated rubrene of Example 1 and 4,4'-[oxalyl bis[[(trifluoromethyl)sulfonyl]imino]ethylene]bis(4-methylmorpholinium trifluoromethanesulfonate. An excellent generation of chemiluminescence occurs.

EXAMPLE 3

Replacing the oxalyl compound of Example 2 with the bis(tetramethylammonium) salt of bis(2,3,6-trichloro-4-sulfophenyl)oxalate again results in the excellent generation of chemiluminescence.

We claim:

1. A process for the production of a sulfonated rubrene which comprises slowly charging an aqueous solution of fuming sulfuric acid to a solution of a rubrene in a solvent mixture of dioxane, and at least one of ethylene dichloride and methylene dichloride, reacting the acid and rubrene for at least about 12 hours, and recovering the resultant sulfonate rubrene.

2. A method according to claim 1 wherein the sulfonate rubrene is recovered by adding water to the reaction media, adjusting the pH to about 7.0, concentrating the resultant aqueous phase, slurrying the resultant concentrated product in an alcohol, filtering the slurry and concentrating the filtered alcohol solution.

3. A method according to claim 2 wherein said alcohol is methanol.

4. A method according to claim 1 wherein said solvent mixture comprises dioxane, ethylene dichloride and methylene dichloride at a ratio of about 2:2:1, respectively.

* * * * *

UNITED STATES PATENT OFFICE
CERTIFICATE OF CORRECTION

Patent No. 4,696,770                         Dated September 29, 1987

Inventor(s) David Louis Dauplaise and William John Trzaskos

It is certified that error appears in the above-identified patent and that said Letters Patent is hereby corrected as shown below:

In Column 1, insert the following statement as the second paragraph of the Specification:

--The invention herein described was made in the course of or under a contract (Contract No. N00014-82-C-0202) or subcontract thereunder, (or grant) with the Office of Naval Research.--

Signed and Sealed this

Twenty-ninth Day of January, 1991

*Attest:*

HARRY F. MANBECK, JR.

*Attesting Officer*          *Commissioner of Patents and Trademarks*